United States Patent [19]
Rivetti et al.

[11] Patent Number: 5,686,644
[45] Date of Patent: Nov. 11, 1997

[54] PROCEDURE FOR THE PRODUCTION OF ALKYL CARBONATES

[75] Inventors: Franco Rivetti, Milan; Ugo Romano, Vimercate, both of Italy

[73] Assignee: Enichem Synthesis S.p.A., Palermo, Italy

[21] Appl. No.: 232,424

[22] Filed: Apr. 21, 1994

Related U.S. Application Data

[63] Continuation of Ser. No. 947,527, Sep. 21, 1992, abandoned.

[30] Foreign Application Priority Data

Sep. 23, 1991 [IT] Italy .................. MI91A02529

[51] Int. Cl.$^6$ .................................................. C07C 69/96
[52] U.S. Cl. ............................................................ 558/277
[58] Field of Search ............................................... 558/277

[56] References Cited

U.S. PATENT DOCUMENTS

| | | | |
|---|---|---|---|
| 5,004,827 | 4/1991 | Curnutt | 558/277 |
| 5,206,409 | 4/1993 | Romano et al. | 558/277 |
| 5,210,269 | 5/1993 | Di Muzio et al. | 558/277 |
| 5,231,213 | 7/1993 | Landscheidt et al. | 558/277 |

FOREIGN PATENT DOCUMENTS

| | | |
|---|---|---|
| 0 354 970 | 2/1990 | European Pat. Off. . |
| 0 366 177 | 5/1990 | European Pat. Off. . |
| 366177 | 5/1990 | European Pat. Off. . |
| 425197 | 5/1991 | European Pat. Off. . |
| 0 445 891 | 11/1991 | European Pat. Off. . |
| 0 460 732 | 12/1991 | European Pat. Off. . |
| 30 16 187 | 10/1981 | Germany . |

*Primary Examiner*—Johann Richter
*Assistant Examiner*—Laura L. Stockton
*Attorney, Agent, or Firm*—Oblon, Spivak, McClelland, Maier & Neustadt, P.C.

[57] ABSTRACT

Dialkyl carbonate is prepared by reacting an alcohol with a gaseous mixture of carbon monoxide and oxygen in the presence of cuprous chloride as catalyst and hydrochloric acid as in situ regenerator of the catalyst.

16 Claims, 1 Drawing Sheet

PROCEDURE FOR THE PRODUCTION OF ALKYL CARBONATES

This application is a Continuation of application Ser. No. 07/947,527, filed on Sep. 21, 1992, now abandoned.

The present invention relates to a procedure for the production of alkyl carbonates.

More specifically the present invention relates to a procedure for the production of alkyl carbonates, and in particular dimethyl carbonate, starting from carbon monoxide, oxygen and an alcohol in the presence of a cuprous halide as catalyst.

Alkyl carbonates are extremely versatile products which are used as organic solvents and as additives for fuels, or as reagents, as a substitute of phosgene, in the synthesis of other useful alkyl or aryl carbonates such as synthetic lubricants, solvents, plasticizers and monomers for organic glass and in methylation and carbonylation reactions for the preparation of isocyanates, urethanes and polycarbonates.

The usual method for preparing alkyl carbonates consists in the reaction of alcohols with phosgene, as described, for example, in Kirk-Othmer, Encyclopedia of Chemical Tecnology, 3a Ed., Vol.4, page 758.

As this procedure has various disadvantages, arising from the use of phosgene, alternative procedures have been devised of which the procedure based on the oxidative carbonylation of an alcohol, in the presence of suitable catalysts, has been particularly successful in the last few years.

The catalysts used in this oxidative carbonylation procedure are generally composed of copper compounds, as described for example in U.S. Pat. Nos. 3,846,468, 4,218, 391, 4,318,862, 4,360,477, 4,625,044, in published European Patent Applications 71.286, 217.651, and in the published German Patent Application 3.016.187.

The most widely-used method at present involves the use of a catalyst composed of cuprous chloride and is essentially based on the following reaction, examplified in the case of dimethylcarbonate.

$$2\ CH_3OH + CO + \tfrac{1}{2}\ O_2 \rightarrow (CH_3O)_2CO + H_2O \qquad (I)$$

The procedure evolves through two phases of oxidation and reduction; without entering into the detailed mechanism of the reaction, it is presumed that in the first step the cuprous chloride reacts with methanol and oxygen to form a cupric methoxychloride which, in the-second step, is reduced by the carbon monoxide with the production of dimethylcarbonate and the regeneration of cuprous chloride $$2CuCl + 2CH_3OH + \tfrac{1}{2}\ O_2 \rightarrow 2Cu(OCH_3)Cl + H_2O \qquad (II)$$

$$2\ Cu(OCH_3)Cl + CO \rightarrow (CH_3O)_2CO + 2CuCl \qquad (III)$$

This process however has a disadvantage due to the fact that the catalyst loses its activity over a period of time because of the loss of chlorine in the form of chlorinated products generated during the reaction.

Published European Patent Applications 134.668 and 413.215 and Italian Patent Application 20530 A/90 describe particular versions of the above procedure wherein the reaction products are continuously removed from the reaction mixture by evaporation induced by the saturation of the flow of gases fed into the reactor (CO, oxygen, possible inert gases).

Even in these processes, however, the problem of a decrease in the activity of the catalyst is not solved.

The Applicant has now found an improved process for the production of alkyl carbonates, and in particular dimethylcarbonate, starting from carbon monoxide, oxygen and alcohol, in the presence of a cuprous halide as catalyst, wherein the catalytic activity is stabilized by the addition of a halogenidric acid into the reaction system without causing any secondary reactions which would lower the yield of dialkylcarbonate.

This result is surprising in that it is well-known that the action of halogenidric acids on alcohols such as methanol or mixtures containing these alcohols, especially when the operating temperatures are higher than the room temperature, cause the formation of high quantities of alkyl halides and/or dialkylethers. In the case of methanol and hydrochloric acid these reactions may be summarized as such:

$$CH_3OH + HCl \longrightarrow CH_3Cl + H_2O \qquad (IV)$$

$$2CH_3OH \xrightarrow{HCl} CH_3OCH_3 + H_2O \qquad (V)$$

The present invention consequently relates to a procedure for the preparation of dialkylcarbonates with a high selectivity and a productivity generally higher than 20 and which can reach about 200 grams of dialkyl carbonate per liter of reactor volume per hour and which remains constant over an indefinite period of time, including:

1. dispersing a carbonylation catalyst composed of a cuprous halide in a reaction medium basically composed of a $C_1$–$C_4$ alcohol;
2. reacting the dispersion thus obtained with a gaseous mixture basically composed of carbon monoxide and oxygen in the presence of a halogenidric acid, wherein the halide is preferably of the same type as the catalyst, to obtain a liquid synthesis mixture basically containing dialkylcarbonate, water and possibly unreacted alcohol;
3. recovering the dialkyl carbonate produced from the synthesis mixture.

According to one of the preferred methods of the procedures of the present invention the synthesis catalyst is composed of cuprous chloride and is preferably dispersed in methanol or ethanol.

BRIEF DESCRIPTION OF THE DRAWINGS

The drawing represents a diagram of the apparatus for the production of dimethylcarbonate.

During the synthesis of the dialkyl carbonate, which can be either a flow or batch process, the molar ratio between carbon monoxide and oxygen is usually higher than that of the stoichiometric value of the reaction and ranges from 3/1 to 100/1, preferably from 20/1 to 100/1, whereas the halogenidric acid, generally hydrochloric acid, is fed in such quantities as to maintain in the catalyst a ratio halogen/copper of about 1.

Figure 1:
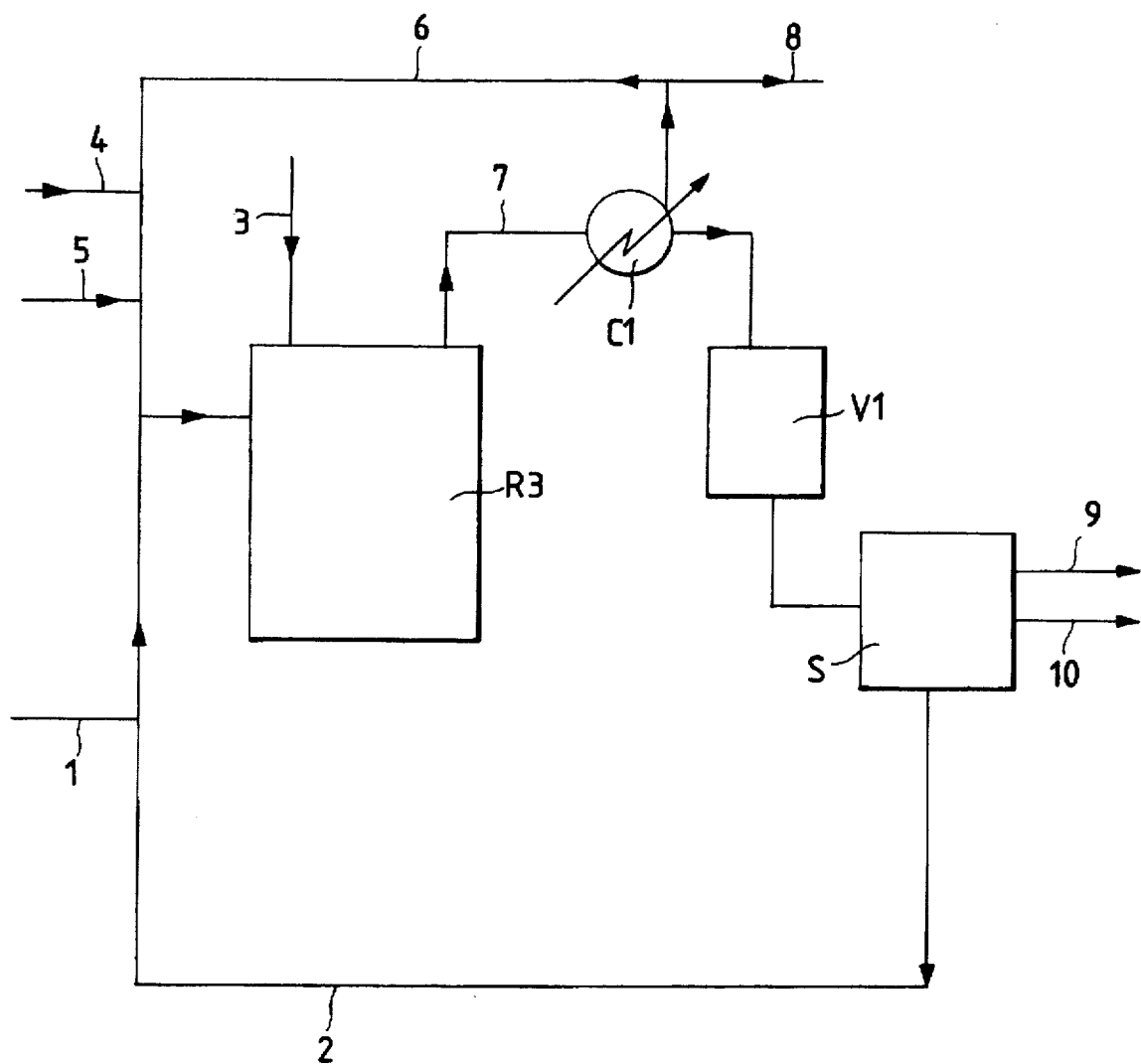

Quantities of acid of between 0.001 and 0.1 moles per mole of dialkyl carbonate produced, are normally used.

In practice the reaction is carried out by dispersing the catalytic system in the reaction medium, basically composed of alcohol possibly mixed with an inert solvent, such as a hydrocarbon, a halogenated hydrocarbon, an ester or ether, and putting this system in contact with the gaseous mixture of oxygen and CO.

The gaseous mixture which is put in contact with the alcohol dispersion, can be obtained either by pre-mixing the carbon monoxide and oxygen or alternatively by feeding the single gases separately and in this latter case contemporaneously or with alternating cycles.

It is also possible to Use gaseous mixtures containing other gases, such as $H_2$, $N_2$, $CO_2$, $CH_4$, which behave as inert gases and do not cause secondary reactions in the reaction system. In particular it may be convenient, as described in U.S. Pat. No. 4,318,862, to use carbon monoxide mixed with hydrogen.

The halogenidric acid may be added to the reaction system in a gaseous phase or as an aqueous or alcoholic solution. In the case of an aqueous solution, the concentration is preferably such as to limit the quantity of water introduced into the system, in that high concentrations of water diminish the selectivity and productivity of the reaction.

The halogenidric acid may be added directly into the synthesis reactor or pre-mixed with the reagents. It can be added either continuously or in batch, preferably continuously.

The reaction is conveniently carried out at temperatures ranging from 50° to 200° C., and, preferably, between 70° and 150° C., at a pressure ranging from the atmospheric value to 100 atmospheres, preferably from 10 to 100 atmospheres and with quantities of catalyst ranging from 10 to 300 g/l of liquid reaction mixture.

With respect to the recovery of the dialkyl carbonate, the conventional separating techniques may be used, such as distillation, filtration, decanting, centrifugation, demixing, absorption on solid absorbents or permeation through selective membranes. These recovery techniques may be used either alone or combined with each other.

The catalytic system and the non-converted reagents, together with any possible variable quantities of dialkyl carbonate and water, may be recycled to the carbonylation reaction.

In a specific version of the procedure of the present invention, in particular for the production of dimethylcarbonate, which follows the general lines already described in the above-mentioned Italian Patent Application 20530 A/90, the separation of the reaction products is carried out in continuous by evaporation caused by the saturation of the flow of gases fed into the reactor. This solution has the advantage of avoiding, in a flow process, the movement and recycling of the catalyst to the synthesis reactor. The addition of hydrochloric acid into the system allows the stabilization, even at the highest possible productivity, of the catalytic system which would otherwise be rapidly deactivated.

In an example of this specific method, the procedure for the preparation in continuous of dimethyl carbonate includes:

a) feeding methanol, hydrochloric acid, carbon monoxide and oxygen into a reaction medium, kept under reaction conditions, basically containing a liquid mixture of methanol, dimethyl carbonate, water and a catalyst based on cuprous chloride;

b) removing a flow of vapours basically composed of methanol, water, dimethyl carbonate from the reaction mixture, said flow being present together with the gaseous flow basically containing carbon monoxide;

c) recovering the water and dimethyl carbonate from the vaporized mixture in a quantity substantially equal to that formed during the reaction and recycling the other components to the reaction environment;

the composition and volume of the liquid mixture, contained in the reaction environment, are substantially kept constant for a period of time, with a concentration of methanol equal to or higher than 30% by weight and with a concentration of water equal to or lower than 10% by weight of the mixture.

More specifically, the concentration of methanol in the reaction mixture may vary from 30 to 80% by weight and the concentration of water from 1 to 10% by weight. In the preferred method the process is carried out with a liquid reaction mixture having a composition within the following value ranges: methanol from 35 to 80% by weight and water from 2 to 7% by weight, the remaining percentage being basically composed of dimethyl carbonate and the inevitable impurities.

The following products are consequently fed in continuous to the above liquid reaction mixture: methanol, hydrochloric acid (possibly aqueous or methanolic), carbon monoxide, fresh and recycled, and oxygen possibly also together with recycled dimethyl carbonate, the quantity of the fresh reagents being substantially equivalent to that converted in the reaction environment, or, with respect to hydrochloric acid, to the quantity of chlorine lost from the catalyst.

The following examples provide a better illustration of the present invention but do not limit it in any way.

EXAMPLE 1 (COMPARATIVE)

3 liters of ethanol and 360 g of CuCl are charged into a internally enamelled reactor equipped with a reflux condenser.

The system pressurized with carbon monoxide at 25 $kg/cm^2$ is brought to a temperature of 135° C. A gaseous flow composed of 260 Nl/hr of carbon monoxide and 25 Nl/hr of $O_2$ are fed into the reactor. A flow of gases composed of non-converted carbon monoxide and oxygen and the $CO_2$ formed as a reaction by-product is released from the reactor, through the reflux condenser, operating under pressure control.

The reaction is interrupted after 4 hours.

After depressurizing the reactor, the liquid reaction mixture contained in the reactor is separated from the catalyst by evaporation under vacuum, collected and analysed.

3 liters of ethanol are freshly charged into the reactor, containing the catalyst used in the previous test, and the reaction is repeated as previously described.

10 reaction cycles are carried out in this way. The following table shows the % by weight of diethylcarbonate (DEC) obtained, in the reaction mixture collected after each single test:

| Test number | % DEC |
|---|---|
| 1 | 23.2 |
| 2 | 19.2 |
| 3 | 18.3 |
| 4 | 16.5 |
| 5 | 14.2 |
| 6 | 13.2 |
| 7 | 12.5 |
| 8 | 10.8 |
| 9 | 9.6 |
| 10 | 9.6 |

EXAMPLE 2

The procedure described in Example 1 is repeated also charging a 37% by weight aqueous solution of hydrochloric acid (HCl), as well as the ethanol, into the reactor at the beginning of the tests, starting from test no.7.

The quantity of acid added and the results obtained are shown in the following table:

| Test number | HCl 37%, cm³ | % DEC |
|---|---|---|
| 1 | — | 22.2 |
| 2 | — | 20.4 |
| 3 | — | 19.1 |
| 4 | — | 16.3 |
| 5 | — | 14.2 |
| 6 | — | 13.3 |
| 7 | 60 | 14.8 |
| 8 | 12.5 | 19.4 |
| 9 | 12.5 | 19.3 |
| 10 | 12.5 | 19.1 |

EXAMPLE 3

The procedure described in Example 1 is repeated but using a 65% mixture of CO and $N_2$ in carbon monoxide instead of pure carbon monoxide and charging HCl into the reaction system in the quantities shown in the Table, which also indicates the results obtained.

| Test number | HCl 37%, cm³ | % DEC |
|---|---|---|
| 1 | — | 14.6 |
| 2 | 15 | 11.1 |
| 3 | 15 | 12.9 |
| 4 | 15 | 13.7 |
| 5 | 15 | 13.3 |
| 6 | 15 | 11.4 |
| 7 | 15 | 12.6 |
| 8 | 15 | 10.4 |
| 9 | 15 | 11.4 |
| 10 | 15 | 13.0 |

EXAMPLE 4

Dimethyl carbonate is produced with a continuous process following the procedure described in Italian Patent Application 20530 A/90.

A diagram of the apparatus used is shown in FIG. (1) where the reactor R3 is an internally enamelled reactor, equipped with a stirrer and a thermal regulation jacket with diathermal oil, containing 10 l of reaction liquid and 2600 g of cuprous chloride catalyst (CuCl) equal to a concentration of 260 g/l. The reactor is pressurized to relative 24 kg/cm² and heated to 130° C.

The following products are fed into the reactor under normal conditions:

970 g/h (line 1) of fresh methanol;

8786 g/h (line 2) of a recycled liquid flow containing 77.3% by weight of methanol and 22.7% by weight of dimethylcarbonate;

15.7 g/h (line 3) of a 37% by weight aqueous solution of hydrochloric acid (5.8 g of 100% HCl);

1160 Nl/h (line 4) of a flow of carbon monoxide having a 93% purity in volume, the rest being composed of inert gases ($H_2$, $N_2$, $CH_4$, Ar);

235 Nl/h (line 5) of oxygen having a 98% purity in volume;

10500 Nl/h (line 6) of a recycled gaseous flow containing carbon monoxide 84% in volume, oxygen 0.7% in volume, carbon dioxide 4.5% in volume, the rest being mainly composed of inert gases.

The composition of the liquid mixture inside the reactor (R3) is the following: methanol 62.9%, dimethylcarbonate 32.2%, water 4.9% by weight.

The flow of gases and vapours leaving the reactor (R3), by line 7 is cooled in the exchanger C1 at about 20° C. and the liquid phase separated from the gaseous phase which goes through line 6, is recycled to the reactor R3 after cleaning with 860 Nl/h (line 8).

10.39 kg/h of a liquid mixture having the following composition are collected in V1: methanol 65.8% by weight, dimethylcarbonate 31.2% by weight, water 2.7% by weight and by-products 0.3% by weight.

1300 g/h of dimethylcarbonate (line 9) and 281 g/h of water (line 10) produced by the reaction are separated by fractionated distillation and demixing in S, whereas a flow of methanol and excess evaporated dimethylcarbonate is recycled through line 2.

From the previous data a 12.4% conversion of the methanol with a molar selectivity to dimethylcarbonate is determined calculated on 96% of methanol. The productivity is equal to 130 g of dimethylcarbonate per liter of solution and per hour.

The reaction is carried out in continuous over a period of 15 days without substantial variations in the standard conditions and productivity.

We claim:

1. A process for the preparation of dialkyl carbonates consisting essentially of:

(a) dispersing a carbonylation catalyst composed of a cuprous halide in a reaction medium comprising a $C_1$–$C_4$ alcohol to obtain a dispersion;

(b) reacting the dispersion thus obtained with a gaseous mixture comprising carbon monoxide, oxygen and a halogenidric acid, wherein the catalytic activity is stabilized by said addition of said halogenidric acid into the reaction system;

wherein the halogenidric acid is hydrochloric acid;

wherein said hydrochloric acid is present in an amount sufficient to maintain in the catalyst a ratio of halogen/copper of about 1; and wherein said ratio is maintained by regulating the amount of said hydrochloric acid introduced into the reactor to obtain a liquid synthesis mixture containing dialkyl carbonate, water and possibly unreacted alcohol;

(c) recovering the dialkyl carbonate produced, wherein said dialkyl carbonate is dimethyl carbonate and wherein the productivity is higher than 20 grams of dialkyl carbonate per liter of reactor volume per hour, which remains substantially constant over an indefinite period of time.

2. The process according to claim 1, wherein the carbonylation catalyst is composed of cuprous chloride and is dispersed in methanol or ethanol.

3. The process according to claim 1, wherein the molar ratio between carbon monoxide and oxygen is higher than the stoichiometric value of the reaction and is between 3/1 and 100/1.

4. The process according to claim 1, wherein the halogenidric acid is fed in quantities ranging from 0.001 to 0.1 moles per mole of dialkylcarbonate produced.

5. The process according to claim 1, wherein the reaction is carried out at temperatures ranging from 50° to 200° C. and at a pressure ranging from atmospheric pressure to 100 atmospheres, with quantities of catalyst ranging from 10 to 300 g/l of liquid reaction mixture.

6. The process according to claim 1, wherein the dialkylcarbonate is recovered by separation techniques selected from distillation, filtration, decanting, centrifugation, demixing, absorption on solid absorbents, and permeation through selective membranes.

7. The process according to claim 1, wherein the halide of the halogenidric acid is the same as the halide of the catalyst.

8. The process according to claim 3, wherein the molar ratio between carbon monoxide and oxygen is between 20/1 and 100/1.

9. A process for the continuous preparation of dimethylcarbonate consisting essentially of:
 (a) feeding methanol, hydrochloric acid, carbon monoxide and oxygen into a reaction mixture containing a liquid mixture of methanol, dimethylcarbonate, water and a catalyst based on cuprous chloride;
 (b) removing a flow of vapours composed of methanol, water, dimethylcarbonate from the reaction mixture, said flow being present together with a gaseous flow containing carbon monoxide; and
 (c) recovering the vaporized water and dimethylcarbonate from the reaction mixture in a quantity substantially equal to that formed during the reaction and recycling the other components to the reaction environment; wherein the composition and volume of the liquid mixture, contained in the reaction mixture, are substantially kept constant over a period of time, with a concentration of methanol equal to or higher than 30% by weight and a concentration of water equal to or lower than 10% by weight in the mixture and wherein the hologenidric acid is fed in such quantities as to maintain in the catalyst a ratio of halogen/copper of about 1 and the productivity is higher than 20 grams of dialkyl carbonate per liter of reactor volume per hour, which remains substantially constant over an indefinite period of time.

10. The process according to claim 9, wherein the concentration of methanol in the reaction mixture varies from 30 to 80% by weight and the concentration of water from 1 to 10% by weight.

11. A process of making dialkylcarbonates consisting essentially of:
 (a) dispersing a cuprous halide catalyst in a reaction medium comprising a $C_1$–$C_4$ alcohol to obtain a dispersion;
 (b) reacting the dispersion with a mixture including CO and $O_2$ in the presence of HX, where HX is hydrochloric acid, to obtain a dialkylcarbonate;
 (c) recovering the dialkylcarbonate wherein said dialkylcarbonate is dimethylcarbonate;
 wherein the amount of HX present is the amount necessary to maintain in the catalyst an overall ratio of X:Cu of about 1:1 and wherein said ratio is maintained by regulating the amount of said hydrochloric acid introduced into the reactor, and wherein the productivity is higher than 20 grams of dialkyl carbonate per liter of reactor volume per hour, which remains substantially constant over an indefinite period of time.

12. The process according to claim 11, wherein the amount of dialkylcarbonate produced is between 1000 and 10 moles per mole of HX used.

13. The process according to claim 12, wherein the catalyst comprises CuCl.

14. The process according to claim 13, wherein the molar ratio between CO and $O_2$ is higher than the stoichiometric value of the reaction and is between 3/1 and 100/1.

15. The process according to claim 14, wherein the reaction is carried out at temperatures ranging from 50° to 200° C. and at a pressure ranging from 1 to 100 atmospheres.

16. The process according to claim 11, wherein the concentration of water is from 1 to 10% by weight.

* * * * *